United States Patent [19]
Robichon et al.

[11] Patent Number: 6,102,940
[45] Date of Patent: Aug. 15, 2000

[54] DEVICE FORMING AN ENDOLUMINAL INTRACORPOREAL ENDOPROSTHESIS, IN PARTICULAR FOR THE ABDOMINAL AORTA

[75] Inventors: Manuel Robichon, St. Cloud; Jean-Jacques Meunier, Paris, both of France

[73] Assignee: Legona Anstalt, Vaduz, Luxembourg

[21] Appl. No.: 09/046,154

[22] Filed: Mar. 23, 1998

[30] Foreign Application Priority Data

Feb. 25, 1998 [FR] France .................. 98 02259

[51] Int. Cl.$^7$ .................. A61F 2/06
[52] U.S. Cl. .................. 623/1
[58] Field of Search .................. 623/1, 12

[56] References Cited

U.S. PATENT DOCUMENTS

| | | |
|---|---|---|
| 3,657,744 | 4/1972 | Ersek . |
| 5,632,772 | 5/1997 | Alcime et al. .................. 623/1 |
| 5,683,449 | 11/1997 | Marcade .................. 623/1 |
| 5,860,998 | 1/1999 | Robinson et al. .................. 606/194 |

FOREIGN PATENT DOCUMENTS

| | | |
|---|---|---|
| 0 461 791 A1 | 12/1991 | European Pat. Off. .................. 623/1 |
| 0783873-A2 | 7/1997 | European Pat. Off. . |
| 0783874-A2 | 7/1997 | European Pat. Off. . |
| 0 808 612 A1 | 11/1997 | European Pat. Off. . |
| 2 743 293 | 7/1997 | France . |
| 2747912-A1 | 10/1997 | France . |
| 1457921 A1 | 2/1989 | U.S.S.R. .................. 623/1 |
| WO 97/33532 | 9/1997 | WIPO . |
| WO 97/40779 | 11/1997 | WIPO . |
| WO 98/07389 | 2/1998 | WIPO . |

*Primary Examiner*—David H. Willse
*Attorney, Agent, or Firm*—Cohen, Pontani, Lieberman & Pavane

[57] ABSTRACT

The invention relates to a device forming an endoluminal endoprosthesis. The device comprises at least a first segment, and upstream from said segment, at a predetermined distance therefrom, it comprises a "fixing" upstream segment made of a biocompatible material so as to be deployable from a closed or non-deployed position for insertion purposes to a deployed working position, the deployed working position being designed to be located in a healthy zone of blood vessel and being separated from the first segment by a predetermined distance defined by links of predetermined length. The invention makes it easy to recatheterize a blood vessel such as the abdominal aorta suffering from an aneurysm.

37 Claims, 4 Drawing Sheets

INVENTION

INVENTION

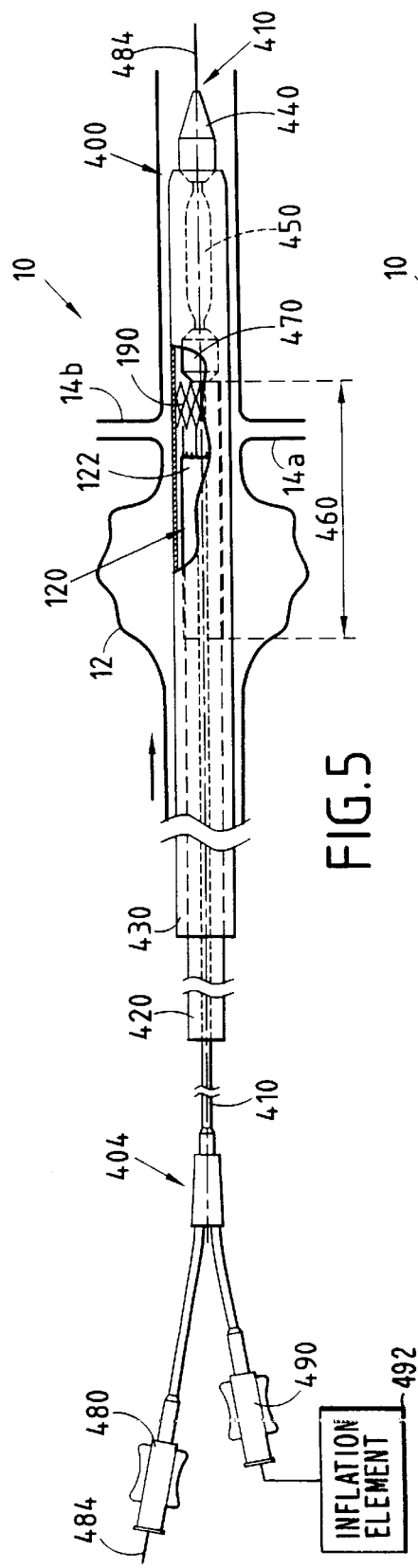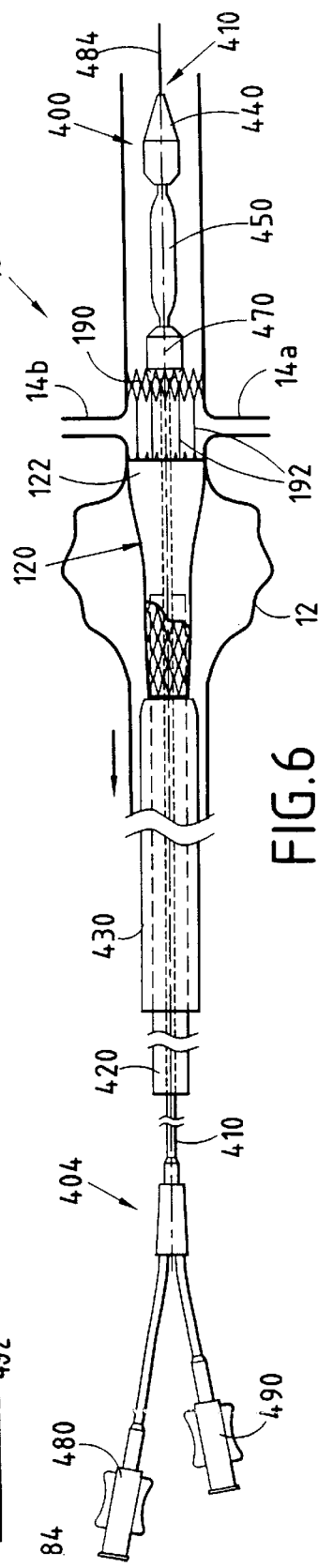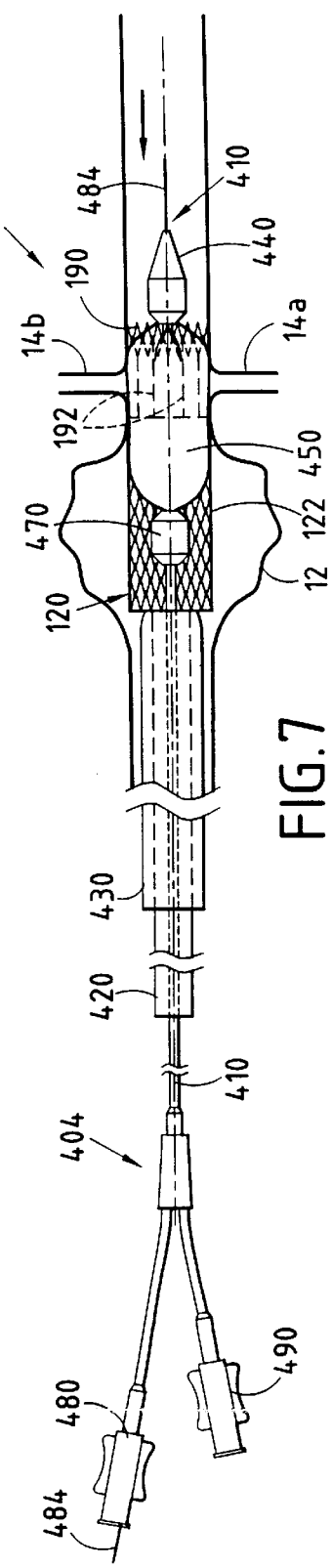

DEVICE FORMING AN ENDOLUMINAL INTRACORPOREAL ENDOPROSTHESIS, IN PARTICULAR FOR THE ABDOMINAL AORTA

The present invention relates essentially to a device forming an endoluminal intracorporeal endoprosthesis, in particular for the abdominal aorta.

BACKGROUND OF THE INVENTION

Devices forming endoluminal intracorporeal endoprostheses are well known to the person skilled in the art, in particular for treating stenoses and above all aneurysms, in particular aneurysms of the abdominal aorta with extension to the femoral arteries in the zone where the femoral arteries branch apart.

For example, document WO 97/33532 contains a very complete description of a device forming an endoluminal prosthesis and the corresponding surgical or therapeutic method, the device comprising a body forming a common trunk and a first limb of great length that penetrates a sufficient distance into the femoral artery, and comprising a small second opening for connection of a second endoluminal endoprosthesis of corresponding small diameter that is designed to penetrate into the second femoral artery.

Such a device presents the following major drawbacks:
a) Because of the small diameter of the opening for connecting the second endoprosthesis to the first endoprosthesis, it is difficult to make this connection because it takes place in a zone suffering from aneurysm where it is easy to insert the second endoprosthesis outside the first endoprosthesis within the aneurysm, such that the practitioner has enormous difficulty in inserting the second endoprosthesis in the opening in the common trunk of the first endoprosthesis.
b) Because the first endoprosthesis necessarily has a first limb incorporated in the device, such a prosthesis can be used only in highly specific clinical circumstances, given the physical conformation of the patient. It is necessary to make several types of endoprosthesis to match the physiological conformations of various patients, and some patients still do not correspond to any endoprosthesis and therefore cannot be treated by this method.
c) Because of the presence of the first limb, the practitioner is obliged to use only one of the two femoral arteries for inserting the endoprosthesis device, and if it is calcified, the operation can no longer be performed.

The Applicant has also made a first invention concerning an endoprosthesis device and described in document FR-A-2 747 912, however it too is incapable of solving those drawbacks.

Likewise, document EP-A-0 783 873 describes a similar endoprosthesis that suffers from the additional drawback of requiring blood flow to be interrupted while it is being put into place, as shown in particular in its FIGS. 24 to 27.

In addition, the endoprosthesis-forming device in the form of a bifurcated stent as described in document EP-A-0 783 873 comprises at least one frustoconically shaped portion for joining to a stent or limb and that suffers from the drawback of creating stenoses.

With reference to its FIGS. 1A and 5, document EP-A-0 783 874 also describes an endoprosthesis-forming device comprising a first segment terminating in two limb starters of frustoconical shape opening out through smaller diameters and in which limb-shaped endoprosthesis-forming devices are positioned that have upstream ends terminating in appropriate frustoconical shapes, as can clearly be seen in FIGS. 6 and 7. That structure suffers from the major drawback due to the fact that positioning the second limb-shaped endoprosthesis device externally is unreliable since there is a risk of it becoming disconnected, in particular under the effect of blood flow. In addition, with that device, installation requires blood flow to be interrupted, as shown clearly in FIGS. 11 to 16.

In addition, as clearly shown in FIGS. 10 to 14, that endoprosthesis needs to have its downstream portion fixed on the low portion of the artery in a healthy region away from the aneurysm.

Document WO 97/40779 discloses a luminal endoprosthesis-forming device for ramification of a duct in the human or animal body comprising a tubular trunk element defining a cavity which is subdivided into a plurality of axial channels over at least a fraction of its length, this being done by inserting a sleeve of flexible biocompatible material into the cavity which is impermeable to body fluids, thereby forming a cavity which is useful for blood flow, and also forming the channels.

In practice, it is necessary to add another tubular trunk element referred to as a "prop" in order to prevent the sleeve of flexible biocompatible material collapsing inside the cavity it defines.

Under such conditions, that prior luminal endoprosthesis requires three distinct elements to be combined in order to achieve proper operation, and that greatly increases the complication of the procedure and the cost of such a device.

Also, and fundamentally, the tubular trunk element is outside the sleeve of flexible material defining the cavity and the channels, such that there is no limit on expansion, so it will deform to match the shape of the aneurysm.

As a result, during X-ray or scanner inspection, the endoprosthesis will take up the shape of the aneurysm and that will not lead to thrombosis of the aneurysm, so in practice no satisfactory treatment of the aneurysm can take place (see FIGS. 2 to 8 of that document, in particular).

OBJECTS AND SUMMARY OF THE INVENTION

Thus, a main object of the present invention is to solve the novel technical problem consisting in supplying a solution for an endoprosthesis-forming device which provides good, non-traumatic, and safe fixing upstream from the prosthesis, without requiring an anchoring device in said upstream portion and also not necessarily requiring fixing of a downstream portion of the prosthesis which can thus be allowed to float freely in the aneurysm, thus making it possible significantly to increase the number of cases of aneurysm that can be treated by the invention, on any mammal and preferably on human beings.

Likewise, an object of the present invention is to solve the novel technical problem consisting in supplying a solution which can make it easy to implant the endoprosthesis itself, and also optionally to connect at least one endoprosthesis device thereto, in particular an endoprosthesis device that is designed to be placed in the femoral artery.

Another object of the present invention is to solve the novel technical problem consisting in supplying a solution which avoids the presence of a first limb in the first endoprosthesis, while still making it possible to obtain clinical results that are the same as those that have been obtained with previously known endoprostheses that have a first limb integrated in the first endoprosthesis.

Another main object of the present invention is to solve the novel technical problem consisting in supplying a solution which enables the endoprosthesis to be inserted via any surgical pathway whether it be the right femoral artery or the left femoral artery, unlike prior devices which require a particular pathway to be used as a function of the initial structure of the basic endoprosthesis having a first limb.

Another main object of the present invention is to solve the novel technical problem consisting in supplying a solution for an endoluminal endoprosthesis-forming device which is usable not only for treating aortic aneurysms in the abdominal zone, but also for performing treatment in any blood vessel such as veins or arteries and regardless of the clinical problems involved, and in particular for treatment of aneurysms or stenoses.

Another main object of the present invention is to solve the novel technical problem consisting in suppling a solution for an endoprosthesis system making it possible to be unaffected by the length of auxiliary endoprosthesis devices, such as stents, for downstream treatment.

Another main object of the present invention is to solve the novel technical problem consisting in supplying a solution for an endoprosthesis-forming device which avoids any problem of crossover between auxiliary devices such as stents, which risk is particularly large when treating an abdominal aorta.

Another main object of the present invention is to solve the novel technical problem consisting in supplying a solution for an endoprosthesis-forming device capable of being fixed at least in part above the renal arteries, without significantly interfering with blood flow in the renal arteries, and to do so in a non-traumatizing manner, without requiring a traumatizing type of anchoring device upstream from the prosthesis, as has generally been necessary in the past.

Another main object of the invention is to solve the novel technical problem consisting in supplying a solution for an endoprosthesis-forming device which is compatible with being installed without interrupting the flow of blood, i.e. without clamping, unlike the prior techniques which, in general, have required blood flow to be interrupted for installation purposes, as shown, for example, in FIG. 24A of document EP-A-0 783 873.

Another object of the present invention is to solve the above-specified technical problems in a manner that is simple, low cost, and usable on an industrial and a medical scale.

Thus, in a first aspect, the present invention provides a device forming an endoluminal endoprosthesis, made at least in part out of a biocompatible material, deployable from a closed or non-deployed position for installation purposes to a deployed working position, comprising at least a first segment, made by construction to be suitable, after deployment, for extending substantially completely across a blood vessel in which it is to be incorporated, the device comprising upstream from said segment, at a predetermined distance therefrom, a "fixing" upstream segment also made of biocompatible material to be deployable from a closed or non-deployed position for installation purposes to a deployed working position, and designed to be placed in a healthy zone of the blood vessel while being separated from the first segment by a predetermined distance defined by links of predetermined length.

Thus, in the event of aneurysm in the abdominal aorta, the upstream segment can be situated above the renal arteries and the first segment is then situated beneath the renal arteries, while the flow of blood, in this case in the renal arteries, is not significantly disturbed. When positioning in the thoracic aorta or in other blood vessels, the upstream segment provides fixing that is safe and reliable for the entire endoprosthesis-forming device of the invention.

In a presently preferred embodiment of the invention, the upstream fixing segment of the endoprosthesis-forming device is made from at least one wire or tape of biocompatible alloy having shape memory, which is preferably the same as the material used for making the first segment. At present, it is advantageous for the upstream segment to comprise only two or three rings of meshwork made by folding or bending a wire or tape in zigzag manner so that each wire defines a ring with each ring thus defining meshwork, the rings of meshwork being interconnected via adjacent bends by appropriate bonding means. This manufacturing technique is well known to the person skilled in the art and is described, for example, in the Applicant's prior document published under the number FR-A-2 747 912 which is incorporated herein in full by reference. In particular, it is advantageous to use a wire that is non-circular in section, in particular a wire that is triangular, square, or rectangular in section.

The above-mentioned bonding means may be constituted either by welding, or preferably by sutures, e.g. as described in FIG. 3 of the Applicant's prior document FR-A-2 747 912.

In another advantageous embodiment of the invention, that is independently patentable on its own, the endoprosthesis-forming device comprises, in addition to the first segment, at least an intermediate second segment, itself comprising at least two independent ducts of smaller diameter than the first segment, each duct having an upstream first opening communicating with the first segment and a downstream second opening communicating with at least a downstream third segment made by construction to be suitable, after deployment, for presenting a diameter that is sufficiently large to be active in said blood vessel, in particular by facilitating possible access and insertion of at least one second endoprosthesis-forming device for the purpose of treating the blood vessel downstream therefrom.

Advantageously, the third segment in the deployed state has a diameter that is substantially equal to the diameter of the first segment in the deployed state.

According to an advantageous characteristic of the device of the invention, it has at least one of its segments and preferably all of its segments, made from at least one wire or tape of biocompatible alloy having shape memory, which alloys are well known to the person skilled in the art. In particular, the wires or tapes may be folded or bent to make up successive rings that are interconnected by bonding means, e.g. as described in the Applicant's prior document published under the number FR-A-2 757 912 which is fully incorporated herein in full by reference. In particular, it is advantageous to use a wire of non-circular section, in particular a wire of triangular, square, or rectangular section. It is also possible to make the device of the invention by a meshwork technique well known to the person skilled in the art.

In another advantageous embodiment of the invention, each of the two said independent ducts of the intermediate second segment is provided by construction to have a diameter in the deployed state that is less than half the diameter in the deployed state of the upstream first segment, so as to leave an empty gap between the two ducts, thereby making it possible to define for each duct a smaller diameter for blood flow, thereby accelerating said flow which promotes better blood flow downstream.

In another advantageous embodiment of the invention, the intermediate segment and/or the downstream third segment is(are) shorter than the upstream segment. The total length of the downstream third segment is preferably no more than about half as long as the upstream segment.

In another advantageous embodiment of the invention, each duct of the intermediate segment is long enough to enable a second endoprosthesis to be positioned for performing downstream treatment, without running any risk of leakage or slipping in the intermediate segment. Preferably, each duct of the intermediate segment is at least about 20 mm long and preferably at least about 30 mm long, the other endoprosthesis devices constituting optionally-insertable stents that are preferably inserted to occupy said intermediate ducts substantially completely, i.e. up to the junction with the first segment.

According to another advantageous characteristic of the invention, the device includes at least one radio-opaque marker element, in particular the first segment includes at its junction with the second segment at least one radio-opaque marker element making it possible to view the positioning of the device and in particular the positioning of the intermediate ducts. These radio-opaque elements are well known to the person skilled in the art and can be made of platinum, for example, which has the advantage of being compatible with use in a blood vessel.

In yet another advantageous embodiment of the invention, said set of segments is manufactured in a single meshworking step using at least one wire so there are no gaps at the junctions between the segments.

In a presently preferred variant embodiment, each segment, including each intermediate duct of the intermediate second segment is made from a bent wire forming substantially annular individual units which are interconnected by appropriate bonding means.

Such bonding means may be constituted either by welds, or preferably by sutures, e.g. as described in FIG. 3 of the Applicant's prior document FR-A-2 747 912. As a result, it is extremely easy to make the intermediate ducts following on from the first segment and also the third segment following on from the intermediate ducts without leaving any gaps between the various segments.

Also, in the context of the present invention, it is possible to make use of the set of advantages provided by the prior solution for an endoprosthesis-forming device described in document FR-A-2 747 912 which is incorporated herein in full by reference. For example, it is possible to provide for only a fraction of the bends of the wires forming the substantially annular individual units to be interconnected by said bonding means such as sutures, thereby imparting greater flexibility to the device when certain joins are not made. Likewise, because the wire used to make the meshwork of the device can be greater in diameter and of non-circular section, advantageously of triangular, square, or rectangular section, it is possible to improve the radial strength of the device very considerably.

In another advantageous embodiment of the invention, the endoprosthesis-forming device comprises, outside said first segment, and advantageously also outside said intermediate second segment and said downstream third segment, an outer protective envelope providing flexible and substantially non-elastic sealing made to have a diameter that corresponds substantially to the diameter in the deployed state of the endoprosthesis-forming device, thereby serving to perform reconstruction proper of the blood vessel. Such substantially non-extensible, flexible, leak-proof envelopes are well known to the person skilled in the art, in particular from the prior art cited in the introduction and also from endoprosthesis devices that are available on the market. These envelopes are often made of polyester film.

In addition, in the context of the invention, it is advantageous for the endoprosthesis-forming device not to be completely covered by said protective envelope that provides sealing, and that therefore reconstructs the blood vessel. Thus, the invention makes it possible to leave uncovered not only the upstream segment, when present, but also an upstream portion of the first segment of the endoprosthesis-forming device, thereby making it possible to impart greater radial strength to the device upstream, thus obtaining a better anchoring effect and avoiding the need to have present an anchoring tooth or lug as is necessary in previously known devices. The device of the invention makes it possible to achieve safe and reliable anchoring while avoiding any risk of sliding and leakage. Manufacturing the device is as easy as in the prior art using conventional meshworking techniques.

By means of the invention, the above-specified technical problems are solved while obtaining a device that is particularly simple, low cost, and usable on an industrial and a medical scale. In addition, the medical procedure for putting the device into position is simplified. The location where the system for installing the endoprosthesis-forming device of the invention is inserted is of no particular importance, and specifically when inserting into the abdominal aorta, the system can make use equally well of the right femoral artery or of the left femoral artery. In addition, the orientation taken up by the endoprosthesis-forming device of the invention in the blood vessel to be treated is of far smaller importance than in the prior art insofar as poor orientation does not prevent the other endoprosthesis-forming devices for downstream treatment, such as stents, being inserted properly, and in particular the danger is avoided of a crossover occurring with the additional devices, such as stents in particular, when they are positioned in the femoral arteries. In the invention, the problem of the prosthesis taking up a wrong orientation is immaterial since the prosthesis does not contain an initial limb, thereby allowing the practitioner subsequently to correctly insert each independent prosthesis such as a limb-forming stent in its proper position and of a length that is appropriate to the clinical conditions involved.

In a second aspect, the present invention also provides a method of surgically treating a blood vessel, the method comprising:

a) providing an endoluminal endoprosthesis-forming device of the invention as defined above; and b) inserting said endoluminal endoprosthesis-forming device in a blood vessel to be treated, in particular to avoid problems associated with aneurysm or stenosis.

Advantageously, the method is implemented without needing to interrupt the flow of blood and advantageously without having to take one particular predetermined access route, in other words either or any route can be used.

In a particularly preferred implementation of the method of the invention, the method is applied to surgical treatment of an aneurysm of the abdominal artery situated upstream from the bifurcation of the aorta towards the femoral arteries.

In yet another advantageous implementation of the surgical method of the invention, the endoprosthesis-forming device of the invention is positioned so that the upstream segment of the device, when present, is positioned in the aorta upstream from the renal arteries, while the upstream end of the first segment of the device bears perceptibly below the renal arteries, thereby making it possible for the endoprosthesis-forming device of the invention to be fixed safely and reliably without trauma and without significantly disturbing the flow of blood in the renal arteries and in the aorta downstream therefrom.

In another advantageous implementation of the method of the invention, an endoprosthesis-forming device is used that has a wide range of diameters in the deployed state, with at least one segment covering the range from 20 mm to 30 mm, thereby making it possible to treat nearly all diameters of aorta, particularly at abdominal level.

In the context of the invention, it is also advantageous to deploy the third segment of the endoprosthesis-forming device at a diameter that is substantially identical to the deployed diameter of the first segment situated upstream, thereby facilitating recatheterization. It is also advantageous for the two ducts of the intermediate segment to present, in the deployed state, a diameter of at least about 9 mm, without any conical shape, thereby avoiding any risk of stenosis.

The devices of the invention are particularly intended for holding blood vessels properly open after stenosis, or for reconstructing or rechanneling blood vessels.

The invention is particularly indicated via a percutaneous route for treatment of occlusive lesions of the peripheral vessels, such as transjugular intrahepatic portosystemic shunt (TIPS); for palliative treatment of biliary occlusions and for treatment of peripheral aneurysms, and in particular for aneurysms of the abdominal and thoracic aortas.

The device of the invention is short, thereby reducing the risk of generating thromboses, providing better urine flow, since this principle can be superposed on conventional vascular prostheses.

Also, because of the wire having a diameter that is advantageously about 0.45 mm, radial strength is increased and the presence of fixing hooks is avoided, thereby reducing the risk of rupturing the wall of the blood vessel (in particular the aorta) and reducing postoperative pain, in particular abdominal pain.

Also, in the context of the invention, the ducts of the intermediate segment are identical and symmetrical about the longitudinal axis of the endoprosthesis-forming device, which is designed to correspond substantially to the longitudinal axis of the blood vessel in which it is inserted, thereby making it possible to adjust better the positioning of each auxiliary endoprosthesis-forming device (often referred to as a secondary branch) relative to the start of the hypergastric arteries, which is a clear departure from the asymmetrical bifurcated systems of numerous prior art devices.

The present invention also makes it possible to reduce difficulties of rechanneling by the guide, and also to reduce the harmful effects of the main part constituted by the above-mentioned first, second, and third segments rotating to a wrong position.

The ducts of the intermediate segment of the invention are circular and not conical in section, thereby avoiding mechanical junction stenoses. These intermediate independent ducts may be up to 25 mm long, or said length may be built up together with the length of the downstream third segment, thereby enabling safe intubation of the main part by the auxiliary devices in endoprostheses 300a, 300b or secondary branches, and avoiding the risk of junction leakage.

BRIEF DESCRIPTION OF THE DRAWINGS

Other objects, characteristics, and advantages of the invention appear clearly in the light of the following explanatory description given with reference to two presently preferred embodiments of the invention given purely by way of illustration and therefore not limiting the scope of the invention in any way. Both embodiments of the invention as shown in FIGS. 3 to 7 form an integral portion of the present invention in all of its aspects.

In the drawings.

Figure 3:
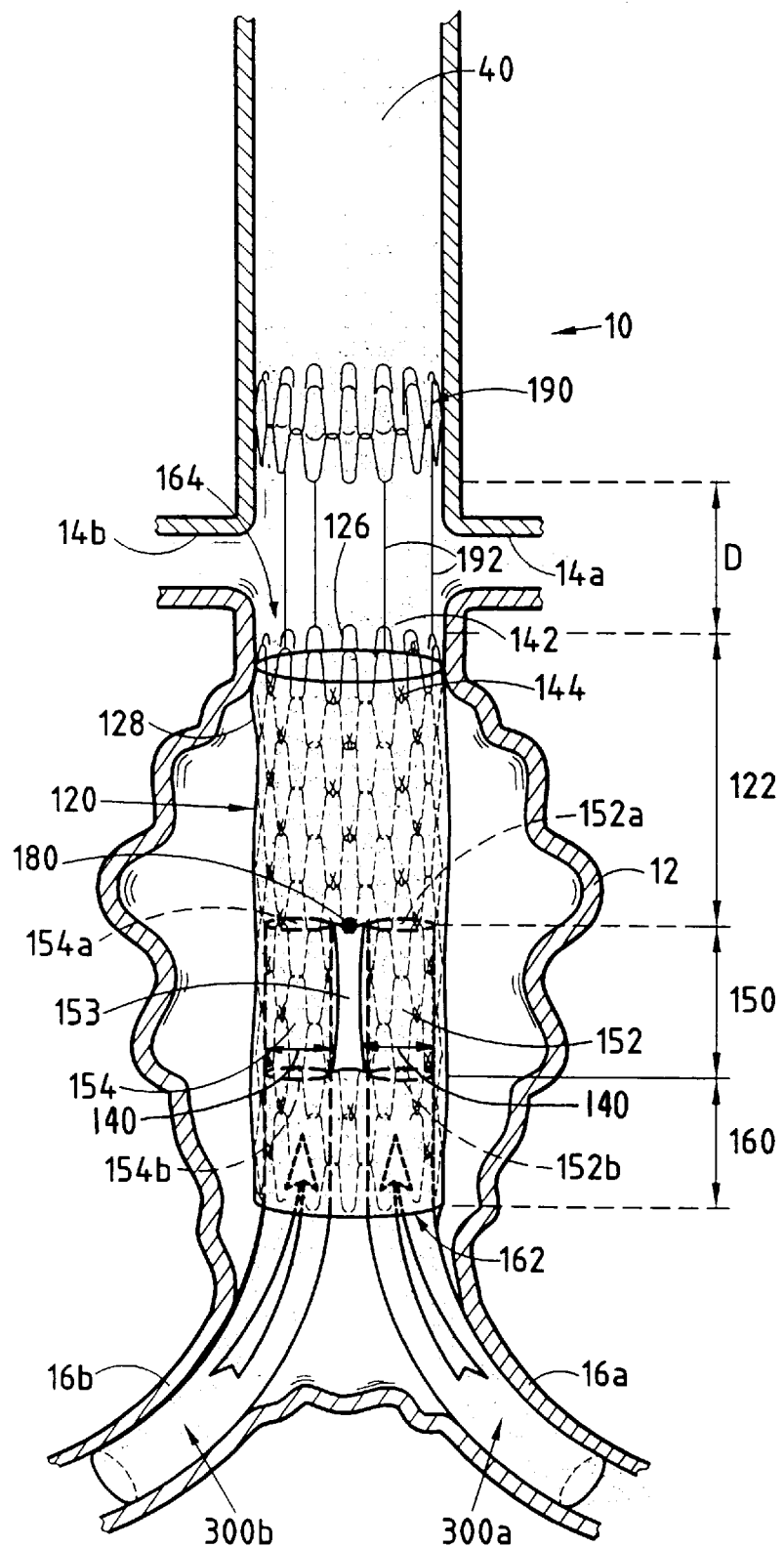
FIG. 3 shows the presently preferred first embodiment of a device of the present invention in which the endoprosthesis-forming device comprises a first segment of prosthesis comprising an upstream segment disposed at a predetermined distance for fixing in the blood vessel upstream from a blood flow branch, in this case upstream from the renal arteries in the abdominal aorta.
Figure 4:
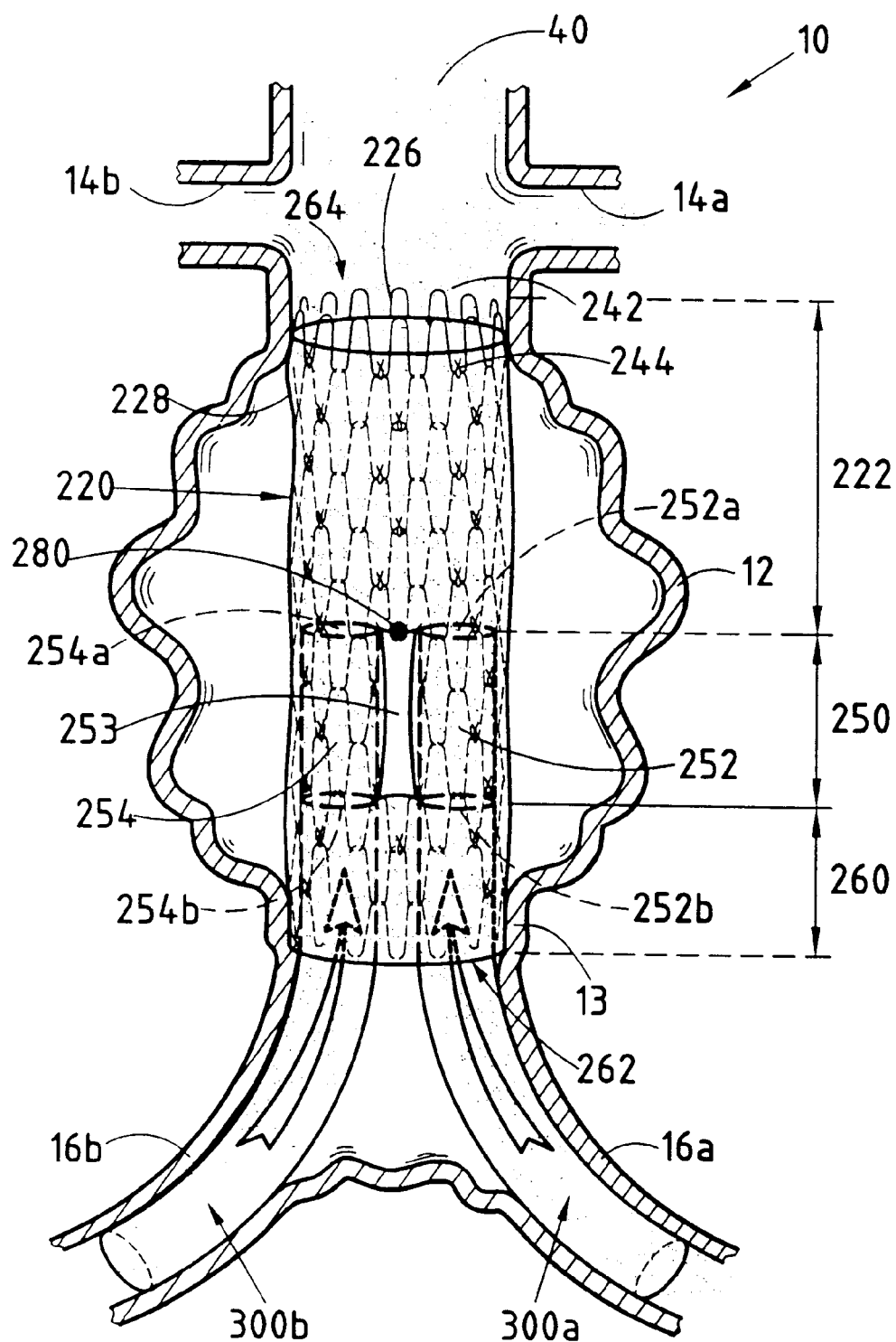
FIG. 4 shows a second embodiment of a device of the present invention in which the upstream segment of FIG. 3 is omitted, showing that the second embodiment can be entirely independent of the embodiment of FIG. 3 and can constitute an independently patentable invention.

In both of the embodiments shown in FIGS. 3 and 4, it is easy to put into place two auxiliary endoprosthesis devices enabling the flow of blood to be diverted into each of the femoral arteries, without any risk of a crossover.

In the drawings:

FIG. 5 is a diagram of the FIG. 3 endoprosthesis-forming device being put into place, showing a first positioning step in which the upstream segment is put into place above the arteries;

FIG. 6 shows a second positioning step, after the first step of FIG. 5, showing how the FIG. 3 endoprosthesis-forming device of the invention is deployed after the outer protective tube has been partially withdrawn; and FIG. 7 shows a third step in putting the FIG. 3 endoprosthesis device into place in the deployed position, prior to completely withdrawing the positioning device and inserting auxiliary endoprosthesis devices enabling the flow of blood to be diverted into each of the femoral arteries in the configuration shown in FIG. 3 and without any risk of crossover; FIG. 7 shows the step in which the balloon is actuated to deploy the endoprosthesis device completely.

MORE DETAILED DESCRIPTION

Figure 1:
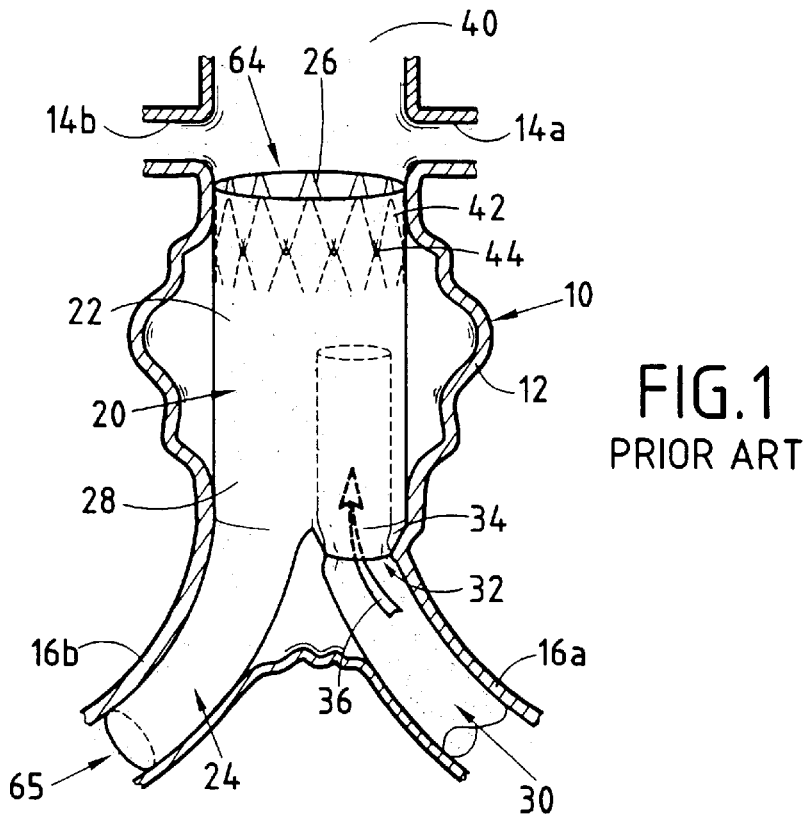
FIG. 1 shows a prior art endoprosthesis-forming device for surgical treatment of aneurysm of the abdominal aorta, e.g. as described in document EP-A-0 783 873 which comprises a first substantial cylindrical segment extended by a limb that penetrates into the femoral artery, together with installation of a second endoprosthesis device enabling a portion of the blood flow to be diverted into the second femoral artery.

With reference to FIG. 1, there is shown diagrammatically and on a greatly enlarged scale a portion of the abdominal aorta given overall reference numeral 10 which has an aneurysm 12 located between the renal arteries 14a, 14b and the femoral arteries 16a, 16b.

In the prior art shown in FIG. 1, which corresponds essentially to document EP-A-0 783 873, provision is made for treating the aneurysm 12 surgically by inserting an endoprosthesis device given overall reference numeral 20, e.g. via femoral artery 16b in this case, which device comprises an upstream first segment 22 integral with a first limb 24. As can clearly be seen from FIG. 1, and as is well known to the person skilled in the art, the endoprosthesis-forming device is made up of two elements, namely: a first element 26 comprising self-expandable meshwork made of a biocompatible wire having shape memory, e.g. of the nitinol type, shown here in the deployed state in the aorta 10 having the aneurysm 12, and covered by an envelope 28 which need cover only a portion of the first element 26, for example and which is generally made of polytetrafluoroethylene or of any biocompatible material capable of providing sealing so as to enable a flow duct to be reconstituted in the aorta towards the femoral arteries 16a and 16b that is leakproof relative to blood flow, as can clearly be understood by the person skilled in the art.

In the prior art, a fraction of the blood flow is diverted into the other femoral artery 16a by inserting another endoprosthesis-forming device 30 such as a simple tubular "stent" that penetrates via an opening 32 defined by a frustoconical portion 34 formed at the downstream end of the first segment 22, with insertion thereof being symbolized by arrow 36 and with the inserted portion thereof being drawn in dashed lines inside the first segment 22 of the endoprosthesis-forming device 20.

It will readily be understood that inserting the second endoprosthesis-forming device 30 is difficult because the opening 32 is narrow and also because of the diameter of the aorta 10 at this location, specifically because of the aneurysm 12, which means there is a high risk of positioning the second endoprosthesis device 30 outside the portion 34 that is in the form of a truncated cone and that has an opening 32 of small diameter.

Figure 2:
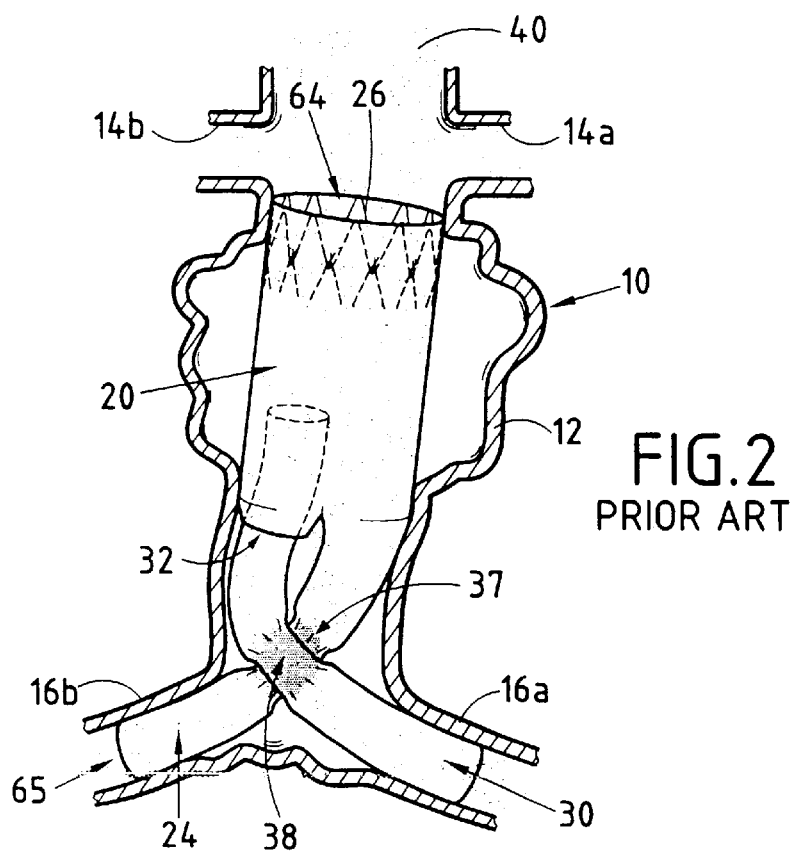
FIG. 2 is a view similar to that of FIG. 1 showing an endoprosthesis-forming device of the same prior art as FIG. 1, but incorrectly positioned, the endoprosthesis-forming device in this case being installed the wrong way round, thereby illustrating the difficulty of inserting a second endoprosthesis device because of the crossover problem.

Also, as can be seen in FIG. 2, it is not uncommon for the endoprosthesis-forming device 20 to be positioned the wrong way round, i.e. with its opening 32 on the same side as the femoral artery 16b via which the first endoprosthesis device 20 having the integral limb 24 was inserted, such that the opening 32 is remote from the other femoral artery 16a.

In this case, in order to be able to cause the second endoprosthesis-forming device 30 to penetrate into the opening 32, it is necessary for it to cross over the first limb 24, which is very difficult to do. Even if the practitioner manages to do it, the limb 24 and the second endoprosthesis device 30 will press against each other in zones 37, 38 shown in FIG. 2, and that is unacceptable given the risk of blood flow being interrupted or of a stenosis being created, particularly between the inlet 64 and the outlet 65.

FIG. 3 shows a presently preferred first embodiment of the invention that is given purely by way of illustration and therefore cannot limit the scope of the invention in any way.

The reference numerals used in describing the invention are the same as those used in describing the prior art device, plus 100, thereby making understanding and comparison easier. Thus, the endoprosthesis-forming device of the invention is given overall reference 120. It comprises a first element 126 made of a biocompatible material having shape memory that can be deployed from a closed or non-deployed position for insertion purposes to a deployed working position as shown. The device further comprises a second biologically compatible element 128 covering a major portion of the first element 126 and constituting an outer envelope that is leakproof to the flow of blood in the blood vessel constituted in this case, for example, by the aorta 10 and which can be implemented in conventional manner, e.g. out of polytetrafluoroethylene, Dacron, polyester, or any equivalent biocompatible material. It should be observed that the second element 128 is shown in axial section only so as to allow the structure of the first element 126 to be seen more clearly.

In the present invention, the endoprosthesis-forming device 120 comprises at least one main first segment given overall reference numeral 122, analogous to the first segment 22 of the prior art device shown in FIGS. 1 and 2, and implemented by a structure which is suitable, after deployment as shown, for substantially completely filling the cross-section of a blood vessel in which it is to be incorporated, in this case the aorta 10, thereby enabling it to capture the entire blood flow 40 via the opening 164, as will readily be understood by the person skilled in the art.

In the present invention, and specifically in this presently preferred first embodiment as shown in FIG. 3, the device further comprises at least one upstream segment given overall reference 190 which is designed to be located in its operating position at a predetermined distance D from the upstream end of the first segment 122. This upstream segment 190 is connected to the first segment 122 by links 192 which may be circumferentially distributed, e.g. at equal spacing from one another, to provide a safe and reliable connection with the first segment 122. These segments may be constituted, for example, by one or more wires of the same type as that used for making the first segment 122, e.g. a metal having shape memory such as nitinol, and they may be of the same diameter or of a different diameter. The length of the links 192 is predetermined so that the upstream segment 190 is disposed above the renal arteries when inserted in the abdominal aorta, and so that the upstream end of the first segment 122 is disposed beneath the renal arteries, thereby securing the endoprosthesis-forming device 120 safely and reliably in place while substantially avoiding any disturbance to the flow of blood towards the renal arteries and towards the downstream end of the aorta.

The upstream segment 190 can be made using one or more portions of meshwork, preferably two or three, obtained by forming a biocompatible wire made of a material having shape memory, such as a nitinol, into a zigzag shape, with adjacent bends being bonded together by bonding means such as welds, or preferably sutures, as is well known to the person skilled in the art. The bonding means may be made of materials other than the material used for making the meshwork, as is also well known to the person skilled in the art, who may refer on this topic to the Applicant's prior patent FR-A-2 747 912 which is hereby incorporated in full, by reference.

By using this upstream segment 190, it is possible to fix the endoprosthesis-forming device 120 safely and reliably in the blood vessel, in this case in particular the aorta, thus making it possible to treat aneurysms 12a that do not benefit from a healthy sub-renal collar as shown in FIG. 3, and the endoprosthesis-forming device may float freely in the aneurysm, as shown in FIG. 3. Under such circumstances, the invention makes it possible to treat many more cases of aneurysm than is possible using prior art endoprosthesis devices.

Furthermore, in the present invention, and in a particular embodiment forming an independently patentable invention, the main portion of the endoprosthesis-forming device 120 comprises, in addition to the first segment 122, at least one intermediate second segment 150 having at least two independent ducts of smaller diameter than the first segment 122 and given respective references 152 and 154. As can clearly be seen in FIG. 3, each of the two independent trunks 152 and 154 is in its own separate trunk having an upstream first opening 152a, 154a in communication with the first segment 122, and a downstream second opening represented by dashed lines 152b, 154b communicating with at least one downstream third segment 160 made of a structure which is suitable, after deployment, for presenting a diameter that is large enough to be active in said blood vessel, in this case the aorta 10, in particular facilitating access and possible insertion via its downstream opening 162 of at least one second endoprosthesis-forming device 300a, 300b for the purpose of treating the blood vessels downstream, as will readily be understood by the person skilled in the art.

Advantageously, in the deployed state, the third segment 160 is of a diameter that is substantially equal to the diameter of the first segment 122 when it is in its deployed state, as shown in FIG. 3. It will thus be understood that the third segment 160 has a very large down-stream opening 162, thus providing easy access for an auxiliary endoprosthesis device, in this case the stents 300a, 300b that are intended to re-catheterize the femoral arteries 16a and 16b, respectively.

According to an advantageous characteristic of the invention, at least one segment, and preferably all three segments 122, 150, 160 are made from at least one wire 42 or tape of shape memory alloy that can be folded to define successive turns forming substantially annular individual units which are interconnected by appropriate bonding means 144 such as welds or preferably sutures, as shown, and as known in particular from the above-mentioned prior art documents, and in particular from the Applicant's document published under the number FR-A-2 747 912.

Thus, any wire or tape of biocompatible alloy having shape memory that is known to the person skilled in the art can be used, for example a nitinol wire. In the context of the invention, it is preferable to use a wire of non-circular section, in particular a wire of section that is triangular, square, or rectangular, and that is of a greater diameter than the diameter which is normally used, e.g. having a diameter of not less than about 0.40 mm, although naturally other diameters may be used without that being limiting.

In another advantageous embodiment of the invention, the bonding means such as the suture knots 144 can be made in various different ways. For example, bonding means 144 need be provided only at some of the bends or turns. It can be advantageous to provide a knot at every other location, as shown in FIG. 3.

Also, in another advantageous embodiment of the invention, each of the two ducts 152, 154 of the intermediate second segment 150 is designed by construction to present in the deployed state, as shown, a diameter that is less than half the diameter in the deployed state of the upstream first segment 122 so as to leave an empty gap 153 between the two ducts 152, 154, thus making it possible in each duct 152, 154 to define a constricted blood flow diameter 140, thereby enabling the flow to be accelerated which is helpful in improving blood circulation downstream in the femoral arteries 16a and 16b.

In yet another advantageous embodiment of the invention, the intermediate segment 150 and/or the downstream third segment 160 is(are) made, as shown, to have a length that is shorter than the length of the first segment 122. The total length of the downstream third segment 160 is preferably equal to no more than about half the length of the first segment 122. Similarly, the total length of the intermediate second segment can be substantially equal to that of the downstream segment 160, even though these lengths can be modified at will without changing the operation of the system, and as a function of surgical requirements made necessary by the physiology of the patient concerned.

In another advantageous embodiment of the invention, the length of each duct 152, 154 in the intermediate segment 150 is sufficient to enable a second endoprosthesis such as 300a, 300b, in this case a stent, to be put into position to provide downstream treatment without running any risk of leakage or slipping in the intermediate segment. In addition, also because of the presence of the third segment 160, each second endoprosthesis such as 300a, 300b is held securely in place, thereby constituting a worthwhile further advantage of the invention.

According to another advantageous characteristic of the invention, the device 120 can have at least one radio-opaque marker element 180, e.g. the upstream first segment 122 may include at its junction with the intermediate second segment 150 at least one radio-opaque marker element such as 180, in this case, making it possible to view the position of the device, and in particular the positions of the intermediate ducts 152 and 154. A radio-opaque element may also be provided upstream from the first segment 122 in the vicinity of the opening 164, and another may be provided at the down-stream end in the vicinity of the opening 162. The marks they provide can be different in shape so as to enable them to be distinguished from one another and so as to facilitate their identification. In addition, the wire 142 is advantageously radio-opaque, as is true of nitinol. By way of example, the radio-opaque elements may be made of platinum which has the advantage of being compatible with use in a blood vessel.

Furthermore, in the context of the invention, because the set of segments 122, 150, and 160 can be made by meshwork and/or knitting at least one wire, manufacture can be performed in a single stage without any gap at the junctions, thus making it possible to avoid any risk of stenosis.

It is then easy to cover the first element which is analogous to a grid 126 with the covering second element 128 or envelope that is made of a bloodproof biocompatible material, such as a film of polytetrafluoroethylene, or of Dacron, or of polyester, or of any other biocompatible material known to the person skilled in the art, for example.

It will be understood that the invention makes it possible to achieve the above-mentioned advantages.

By way of example, the device of the invention can be made using a nitinol wire of square or rectangular section having a diameter of about 0.40 mm, with each segment in the deployed state having a spread over a wide range of diameters going from 20 mm to 30 mm, thereby making it possible to treat blood vessels of nearly all diameters, and in particular aortas, at least at abdominal level.

In the deployed state, the two intermediate ducts 152 and 154 may have a diameter of about 9 mm, and need not have any conical portions, as can clearly be seen in FIG. 3.

Furthermore, the length of the first segment 122 may be as much as 30 mm, such that the intermediate ducts 152 and 154 may be 15 mm long and the downstream third segment 160 may likewise be at least 15 mm long.

By way of example, the invention makes it possible to insert secondary endoprosthesis devices 300a and 300b such as stents that are of different lengths and diameters in each of the femoral arteries 16a and 16b, for example having, in the deployed state, a diameter of 14 mm and a length of 125 mm in the femoral artery 16a, and a diameter of 12 mm and a length of 110 mm in the femoral artery 16b.

It will thus be understood that in the context of the invention, it is possible to make limitless adaptations to different morphological profiles between femoral arteries.

It will thus be understood that all of the advantages of the invention can be obtained regardless of the total length of the endoprosthesis-forming device 120.

As shown, provision may also be made for the envelope 128 to be present over a portion only of the height of the endoprosthesis-forming device 120, and in particular for it to leave uncovered the upstream top portion of said first segment 122 over several millimeters, thereby making it possible in combination with at least one bond on every other mesh to improve the flexibility and the radial strength of the first grid-shaped element 126, at least at its upstream end, and preferably at both ends, in addition to the fixing effect obtained with the upstream segment 190.

Similarly, in the context of the method of surgical treatment of the invention, it is advantageous for the second endoprosthesis devices 300a and 300b, such as stents, to be inserted into the first endoprosthesis device 120 substantially as far as the junction plane between the first segment 122 and the second segment which comprises the two independent intermediate ducts 152 and 154, as shown.

With reference to FIG. 4, there can be seen a second embodiment of the invention, likewise given by way of illustration and thus not in any way limiting the scope of the invention. This second embodiment as shown in FIG. 4 differs from that of FIG. 3 solely by the fact that no upstream segment such as 190 is provided connected at a predetermined distance from the first segment 122 by link means 192 of predetermined length. In this second embodiment, the same reference numerals are used for portions that are identical or similar to those of the FIG. 3 embodiment, plus 100, so in this second embodiment the endoprosthesis-forming device is given overall reference 220. It comprises a first element 226 analogous to the first element 126 of the FIG. 3 embodiment, and a second element 228 analogous to the second element 128 constituting the outer envelope that is proof against the flow of blood 40 in the blood vessel and serving specifically for the purpose of reconstructing it.

In this case, the first segment is given reference numeral 222, the intermediate second segment is given overall reference numeral 250, and the downstream third segment is given overall reference numeral 260, etc.

However, the auxiliary endoprosthesis devices 300a and 300b have the same reference numerals as before since they are independent from the endoprosthesis-forming devices proper.

It can also clearly be seen from FIG. 4, when viewed in comparison with FIG. 3, that the second embodiment is advantageously used with aneurysms 12 that retain a healthy collar in the zone 13 against which the downstream portion of the downstream third segment 160 can bear when it is in the deployed state, as shown in FIG. 4, thus ensuring that the endoprosthesis-forming device 220 is held safely and reliably in place, thereby providing effective treatment for the aneurysm 12.

It will thus be understood that the invention also makes it possible to provide an effective solution to the technical problems specified above and gives rise to substantially the same advantages as the embodiment of FIG. 3.

With reference to FIGS. 5 to 7, there follows a description of the procedure for putting the endoprosthesis-forming device of the present invention into place, which procedure is equally applicable to the embodiment of FIG. 3 and to the embodiment of FIG. 4.

In this context, an inserter 400 is used made up of an inner carrier catheter 410, a pusher sheath 420 sliding over the carrier catheter 410, and an outer sheath 430. The inner carrier catheter 410 is a tube having two lumens, comprising an expander nose 440 having a radio-opaque distal portion immediately followed by an expansion balloon 450, e.g. made of latex, and then a zone 460 serving as a space for positioning the endoprosthesis-forming device 120 or 220 of the invention, defined by a radio-opaque olive-shaped piece 470 and the pusher sheath 420. The proximal portion 404 is constituted by a Y-coupling having two "luer lock" type connection devices of the female type given respective references 480 and 490.

The first "luer lock" 480 serves to pass a guide, e.g. having a diameter of 0.035 inches with a short transparent connection, enabling a metal rod 484 to be inserted into its lumen to hold said path straight without any risk of kinking.

The second "luer lock" 490 serves to connect a tubular inflation element 492 for inflating the balloon 450, e.g. having a connection with long branches. The outer sheath 430 covers a portion of the expander nose 430, the balloon 450, the gap zone 460 for supporting the endoprosthesis-forming device 120 or 220 of the invention, and a portion of the pusher sheath 420.

These devices can have a working length of 500 mm for a total length of 1200 mm and a maximum diameter of 20 F, or a working length of 650 mm for a total length of 1350 mm and a maximum diameter of 23 F.

The technique whereby the endoprosthesis device of the invention is put into place is described below with reference to FIGS. 5 to 7 and in association with FIG. 3.

It is known that aneurysms of the abdominal aorta extend vertically to a greater or lesser extent, coming close or not so close to the renal arteries and to the hypogastric arteries (not shown in FIGS. 3 and 4), thus determining whether it is possible to use an endoprosthesis-forming device of the type of the invention. The other important factor is the possibility of gaining access to the aorta via the femur, and in the present state of the art that requires patients to be selected having iliac arteries that are not too small, i.e. not less than 7 mm, which do not have stenoses, and which are not too tortuous.

Under ideal circumstances, patients having an aneurysm with a long collar, whose iliac arteries are normal and have expanded little, i.e. having a diameter no greater than 14 mm to 16 mm, are good candidates since release is easier proximally and circulation in the pelvis is preserved more easily while avoiding any risk of covering the hypogastric arteries.

The patient is advantageously prone on the back and under anesthetic, or under local or regional anesthetic, such as a peridural or even a local potentialized anesthetic, perfused while monitoring arterial pressure via a radial catheter, and with a urinary probe in place.

A marked radio-transparent ruler is provided which is positioned in such a manner as to identify the release position.

The first step of the procedure is to provide access via the femur on the side having the iliac artery that appears to be the larger and the straighter, given that "reasonable" twisting is not a complete bar.

In a second step, an incision is made and a guide is inserted into the abdominal aorta.

Thereafter, a 6 F or 7 F inserter is put into place and a front aortography is performed using a probe, e.g. of the graduated "pigtail" type, if possible. Thereafter, the positions of the renal and femoral and possibly the polar arteries are identified as are the positions of the hypogastric arteries.

It is also advantageous to perform heparinization, e.g. at 5000 international units, possibly repeated with a half-dose (2500 IU) if the installation procedure is lengthy.

A super-stiff guide can be put into place in the thoracic aorta and in the abdominal aorta (not shown in the figures), and then a transverse femoral arteriotomy is performed preferably in a flexible arc and the main part of the inserter 400 having a diameter of 20 F is inserted, including the endoprosthesis-forming device 120 or 220 on the carrier catheter 410.

The inserter 400 is then raised until the endoprosthesis-forming device 120 or 220 is in register with the ideal release zone as identified on the graduated ruler or by an opaque object in the position shown diagrammatically in FIG. 5.

Thereafter the main body is progressively released, possibly beginning by release 1 cm above the selected zone, and then lowering the prosthesis inserter assembly. The prosthesis body 120 or 220 is released by establishing a fixed point using the internal pusher 420 and withdrawing the outer sheath 430, thereby releasing the prosthesis 120 or 220. As shown diagrammatically in FIG. 6, the prosthesis expands because the material having shape memory, such as nitinol, is heated.

It will be observed that for the embodiment of FIG. 3, the endoprosthesis-forming device 120 has an upstream segment 190 whose release point is designed to be above the renal arteries 14*a* and 14*b*, such that the first segment 122 of the main body of the endoprosthesis-forming device 120 is situated beneath the renal arteries 14*a* and 14*b*, thus achieving safe and reliable fixing of the endoprosthesis-forming device in the blood vessel, in this case the abdominal aorta, and without there being any need for the downstream portion of the endoprosthesis-forming device 120 to be held in place. It will be observed with reference to FIG. 3 that this downstream portion is floating in the aneurysm.

Once the endoprosthesis-forming device 120 has been completely released, the practitioner then lowers the latex balloon 450 at least into the upstream segment 190 of the endoprosthesis-forming device 120 and inflates the balloon at low pressure so as to press the endoprosthesis-forming device 120 properly against the wall of the aorta, mainly level with the upstream segment 190 and advantageously level with the uncovered portion towards the opening 164 so as to ensure safe and reliable fixing against the wall of the blood vessel, in this case the aorta 10.

This expansion may also be performed in the first segment 122 and in the segments 150 and 160, corresponding to the inflation step as shown in FIG. 7.

The person skilled in the art will understand that to achieve proper release, with the intermediate ducts 152 and 154 properly oriented in the frontal plane, it is important to align the radio-opaque markers situated in the proximal portion of the covering and to observe clearly the clips which represent the bifurcations proper, so as to observe the radio-opaque marker 180 constituted in this case by an upside-down V at this level.

Release of the body is then continued by withdrawing the sheath, and the two ducts 152, 154 of the intermediate segment 150 are released.

It is then possible to expand at least one lateral duct 152 or 154 using the latex balloon and to withdraw the main inserter having a diameter of 20 F.

Aortography can then be performed to observe the position relative to the renal arteries 14*a*, 14*b*.

The following stage consists in inserting from the same side the device constituting the auxiliary endoprosthesis, e.g. in this case 300*b*, which constitutes at least one lateral extension of diameter and length that has been determined by pre-operative angiography and 3D scanning, and that may possibly be conical.

It is then possible to raise an inserter having valves with a maximum diameter of 14 F, depending on the diameter of the already-positioned endoprosthesis-forming device 120 or 220, and to position the sheath broadly in the aorta upstream from the renal arteries 14*a*, 14*b*.

Thereafter, the support device, commonly referred to as a "cartridge" is raised, containing the auxiliary endoprosthesis device such as 300*a* or 300*b* and it is engaged in the installed inserter device, and then using the pusher, the auxiliary endoprosthesis device 300*a* or 300*b* is advanced until the proximal markers of the auxiliary device 300*a* or 300*b* become superposed with those identifying the bifurcation, such as 180.

Thereafter the sheath is withdrawn and the device constituting the auxiliary endoprosthesis 300*a*, 300*b* is released, with an overlap of about 2 cm in the ducts 152, 154 of the intermediate segment 150 and of the downstream segment 160. The bottom end of the device forming the auxiliary endoprosthesis 300*a* or 300*b* must naturally not cover the hypogastric arteries.

If length is wrongly calculated, positioning can be modified and the overlap zone may possibly be shorter.

Thereafter it is possible to perform an aortography to check that the limb-forming auxiliary endoprosthesis device 300*a*, 300*b* is properly positioned and that the main endoprosthesis device 120 or 220 is likewise properly positioned.

Thereafter, an incision is made into the femoral artery on the other side and in the same manner, a guide is raised to catheterize the second short auxiliary endoprosthesis device 300*b* or 300*a* on the other side, making use of a catheter of the vertebral type, or of some other type, depending on the morphology of the aorta.

If it is not possible to catheterize the limb on the other side, it is possible to perform insertion the other way, or via the humerus, passing the guide into the iliac artery, which remains to be covered and while recovering the guide in the femur by means of a lasso, a biopsy clamp, or by arteriotomy.

Thereafter, the position of the guide is verified by inserting the "pigtail" type probe into the auxiliary endoprosthesis device 300*b* or 300*a*, or limb, to verify its position by rotating the probe.

Thereafter, the guide can be exchanged with a super-stiff element and raising on the guide, either via an incision or after the femoral artery of the extension which is released in the same manner as the lateral device.

Thereafter, it is possible to perform an arteriography by reflux and using the injector.

Angioplasty by a balloon of diameter adapted to the diameter of the auxiliary endoprosthesis device 300*a*, 300*b* can be implemented in such a manner as to ensure that the two auxiliary prostheses are properly expanded in the overlap zone where they join the main artery endoprosthesis device 120, 220.

Thereafter the femoral arteriotomy is closed.

In the event of distal leakage persisting or of a limb that is too short being provided by the auxiliary endoprosthesis device 300*a*, 300*b*, it is possible to perform a distal extension using the same technique.

The result is considered as being satisfactory if the endoprosthesis-forming device is properly deployed, harmoniously, and if there is no opacification of the aorta aneurysm by proximal or distal leakage.

In addition, when the iliac artery is too sinuous, having a stenosis or carrying a large aneurysm including the hypogastric artery, it is possible to perform a combined technique of placing an endoaortic prosthesis of the invention that is covered and that has degressive conical shape to use an aortomono-iliac access route associated with a femur-femur cross-over bypass, and either a ligature or an opposite side iliac artery occlusion by ambolization.

By means of the invention, is it possible to treat more patients, since ideal or favorable conditions are to be found in 15% to 20% of patients, and when using the combined technique, it is possible to treat between 50% to 75% of patients having an aneurysm in the abdominal aorta.

Finally, in aneurysms of the abdominal aorta having a short proximal collar that is less than 15 mm long, the inventors have discovered that the upstream position of the endoprosthesis-forming device 120 or 220 can be achieved trans-renally, the uncovered upstream portion being capable of being situated without obvious damage upstream from the renal arteries 14a, 14b, as shown in the embodiment of FIG. 3.

The invention also makes it possible to perform a technique of placing an endo-aortic prosthesis in aneurysms of the thoracic aorta.

In which case, the technique is very close to that of releasing the endoprosthesis-forming device when treating an aneurysm of the abdominal aorta as described above.

Firstly, a femoral or iliac approach is provided using a release system having a diameter of 20 F or 23 F.

It is also possible to use a super-stiff type guide and to raise a graduated "pigtail" type probe.

The extent of the aneurysm is identified from the left subclavicular artery or the celiac artery depending on the location of the aneurysm in the thoracic aorta.

The carrier device is raised after heparinization and arteriotomy.

The markers are positioned at the beginning of release 1 cm to 2 cm upstream from the predetermined proximal zone.

The prosthesis is partially released over at least one-third of its length, and it is then accurately positioned.

Thereafter, the sheath is completely withdrawn and the prosthesis is released in full.

The impact of the latex balloon and inspection arteriography is still performed to guarantee that placing has been done properly.

It will thus be understood that the invention makes it possible to solve the various problems specified above in a manner that is simple, safe, and reliable, and that can be used on an industrial and a medical scale.

We claim:

1. An endoluminal endoprosthesis device comprising:

a first element deployable from a closed, non-deployed position for installation purposes to a deployed, working position and having an upstream end and a downstream end, said first element comprising a first segment having first and second end openings and sized for filling a cross-section of a blood vessel in which said first element is to be incorporated when said first element is in said deployed, working position, said first element further comprising a second segment connected to one of said first and second end openings of said first segment and forming at least two independent trunks, each of said at least two independent trunks having an upstream first opening communicating with said first segment and a downstream second opening, said first element further comprising a third segment connected to and communicating with said downstream second opening of said each of said at least two independent trunks of said second segment, said third segment having a diameter in said deployed state for facilitating access of a second endoprosthesis-forming device through said third segment into engagement in one of said at least two independent trunks for treating a blood vessel downstream therefrom, said first element comprising at least one of a wire and tape, wherein said at least one of said wire and tape is made of a biocompatible alloy having shape memory, and said first, second, and third segments being formed by a continuous one of a single meshworking step and a single knitting step of said at least one of a wire and tape such that there are no gaps between the first segment and the second segment and between said second segment and said third segment; and a second element comprising a leak-proof envelope substantially surrounding said first element including said at least two independent trunks of said second segment, said envelope providing a leak-proof fluid seal about said first element and permitting fluid flow from said upstream end to said downstream end of said first element.

2. The device of claim 1, wherein said diameter of said third segment is substantially equal to a diameter of said first segment.

3. The device of claim 1, wherein said third segment is shorter in length than said first segment.

4. The device of claim 1, wherein said first segment is equal in length to or greater than twice said third segment.

5. The device of claim 1, wherein each of said at least two independent trunks is sized for receiving said second endoprosthesis-forming device and effecting a leak-free and non-slip connection therebetween.

6. The device of claim 1, further comprising a radio-opaque marker element mounted at an upstream end of said second segment for facilitating viewing of a position of said second segment.

7. The device of claim 1, wherein said at least one of said wire and tape comprises a bent wire forming substantially annular units, each of said annular units having a plurality of bends, said first, second, and third segments comprising bonding means for connecting said annular units.

8. The device of claim 7, wherein a fraction of the plural bends are connected by said bonding means for facilitating a greater flexibility of said annular units.

9. The device of claim 7, wherein said wire has a non-circular cross-section.

10. The device of claim 1, wherein each of said at least two independent trunks has a constricted blood flow diameter in the deployed state less than half of a diameter of the first segment in the deployed state for facilitating an accelerated blood flow through said second segment thereby promoting increased downstream bloodflow.

11. The device of claim 1, further comprising a fixing segment for connection of said first element to a healthy portion of a blood vessel upstream of said first element and separated from said first element by links of a predetermined length.

12. The device of claim 11, wherein said fixing segment comprises at least another one of a wire and tape, wherein said at least one of another wire and tape is made of a biocompatible alloy having a shape memory.

13. The device of claim 12, wherein said fixing segment comprises a number of rings, the number being within a range including 1 to 3, each of said rings comprising said one of a wire and tape of a biocompatible material bent into a zigzag form and bonding means for connecting adjacent bends of adjacent ones of said rings.

14. The device of claim 1, wherein said envelope does not cover said first element at areas proximate said upstream end and said downstream end of said first element, thereby facilitating connection of said device to the blood vessel of the patient.

15. The device of claim 1, wherein each of said first, second, and third segments is deployable to any overall diameter within a range including 20 to 30 mm.

16. An endoluminal endoprosthesis device comprising:
a first element deployable from a closed or non-deployed position for installation purposes to a deployed, working position and having an upstream end and a downstream end, said first element comprising a first segment having first and second end openings and sized for filling a cross section of a blood vessel in which said first element is to be incorporated when said first element is in said deployed, working position, said first element further comprising a second segment connected to one of said first and second end openings of said first segment and forming at least two independent trunks, each of said at least two independent trunks having an upstream first opening communicating with said first segment and a downstream second opening, said first element further comprising a third segment connected to and communicating with said down stream second opening of said each of said at least two independent trunks of said second segment, said third segment having a diameter in said deployed state for facilitating access of a second endoprosthesis-forming device through said third segment into engagement in one of said at least two independent trunks for treating a blood vessel downstream from said one of said at least two independent trunks, said first element comprising at least one of a wire and tape, wherein said at least one of said wire and tape is made of a biocompatible alloy having a shape memory, and said first, second, and third segments being formed by a continuous one of a single meshworking step and a single knitting step of said at least one of a wire and tape such that there are no gaps between the first segment and the second segment and between said second segment and said third segment;
a second element comprising a leak-proof envelope surrounding said first element including said at least two independent trunks of said second segment, said envelope providing a leak-proof fluid seal about said first element and permitting fluid flow from said upstream end to said downstream end of said first element; and
a fixing segment for connection to a healthy portion of a blood vessel upstream of said first segment of said first element and separated from said first segment by links of a predetermined length.

17. The device of claim 16, wherein said diameter of said third segment is substantially equal to a diameter of said first segment.

18. The device of claim 17, wherein said third segment is shorter in length than said first segment.

19. The device of claim 16, wherein said first segment is equal in length to or greater than twice said third segment.

20. The device of claim 16, wherein each of said at least two independent trunks is sized for receiving said second endoprosthesis-forming device and effecting a leak-free and non-slip connection therebetween.

21. The device of claim 16, further comprising a radio-opaque marker element mounted at an upstream end of said second segment for facilitating viewing of a position of said second segment.

22. The device of claim 16, wherein said at least one of said wire and tape comprises a bent wire forming substantially annular units, each of said annular units having a plurality of bends, said first, second, and third segments comprising bonding means for connecting said annular units.

23. The device of claim 22, wherein a fraction of the plural bends are connected by said bonding means for facilitating a greater flexibility of said annular units.

24. The device of claim 22, wherein said wire has a non-circular cross-section.

25. The device of claim 16, wherein said fixing segment comprises at least another one of a wire and tape, wherein said at least another one of said wire and tape is made of a biocompatible alloy having a shape memory.

26. The device of claim 25, wherein said fixing segment comprises a number of rings, the number being within a range including 1 to 3, each of said rings comprising said at least another one of a wire and tape bent into a zigzag form and bonding means for connecting adjacent bends of adjacent ones of said rings.

27. The device of claim 16, wherein said envelope does not cover said first element at areas proximate said upstream end and said downstream end of said first element, thereby facilitating connection of said device to the blood vessel of the patient.

28. An endoluminal endoprosthesis device comprising:
a first element deployable from a closed or non-deployed position for installation purposes to a deployed working position and having an upstream end and a downstream end, said first element comprising a first segment having first and second end openings and sized for filling a cross-section of a blood vessel in which said first element is to be incorporated when said first element is in said deployed, working position, said first element further comprising a second segment connected to one of said first and second end openings of said first segment and forming at least two independent trunks, each of said at least two independent trunks having an upstream first opening communicating with said first segment and a downstream second opening, each of said at least two independent trunks having a constricted blood flow diameter in the deployed state that is less than half of a diameter of the first segment in the deployed state for facilitating accelerated blood flow through said second segment thereby promoting increased downstream bloodflow, said first element further comprising a third segment connected to and communicating with said down stream second opening of said each of said at least two independent trunks of said second segment, said third segment having a diameter in said deployed state for facilitating access of a second endoprosthesis-forming device through said third segment into engagement in one of said at least two independent trunks for treating a blood vessel downstream from said one of said at least two independent trunks, said first element comprising at least one of a wire and a tape, wherein said at least one of said wire and tape is made of a biocompatible alloy having a shape memory, said first, second, and third segments being formed by means of a continuous one of a single meshworking step and a single knitting step of said at least one of said wire and tape such that there are no gaps between said first and second segments and said second and third segments; and a second element comprising a leak-proof envelope surrounding said first element and said at least two independent trunks of said second segment, said envelope providing a leak-proof fluid seal about said first element and permitting fluid flow from said upstream end to said downstream end of said first element.

29. The device of claim 28, wherein said at least one of said wire and said tape comprises a bent wire forming substantially annular units, each of said annular units having a plurality of bends, and said first, second, and third segments comprising bonding means for connecting adjacent ones of said annular units.

30. The device of claim 29, wherein a fraction of the plural bends are connected by said bonding means for facilitating a greater flexibility of said annular units.

31. The device of claim 29, wherein said wire has a non-circular cross-section.

32. The device of claim 28, further comprising a fixing segment for connection of said first element to a healthy portion of a blood vessel upstream of said first element and separated from said first element by links of a predetermined length.

33. The device of claim 32, wherein said fixing segment comprises at least another one of a wire and tape, wherein said at least one of another wire and tape is made of a biocompatible alloy having a shape memory.

34. The device of claim 33, wherein said fixing segment comprises a number of rings, the number being within a range including 1 to 3, each of said rings comprising said one of a wire and tape of a biocompatible material bent into a zigzag form and bonding means for connecting adjacent bends of adjacent ones of said rings.

35. The device of claim 28, wherein said envelope does not cover said first element at areas proximate said upstream end and said downstream end of said first element, thereby facilitating connection of said device to the blood vessel of the patient.

36. The device of claim 16, wherein each of said first, second, and third segments is deployable to any overall diameter within a range including 20 to 30 mm.

37. The device of claim 28, wherein each of said first, second, and third segments is deployable to any overall diameter within a range including 20 to 30 mm.

* * * * *